United States Patent [19]

Olvey et al.

[11] Patent Number: 5,141,552

[45] Date of Patent: * Aug. 25, 1992

[54] METHOD OF HYBRIDIZING COTTON

[75] Inventors: James M. Olvey, Phoenix, Ariz.; Harold L. Lindaberry, Ambler, Pa.

[73] Assignee: University Patents, Inc., Westport, Conn.

[*] Notice: The portion of the term of this patent subsequent to May 5, 2009 has been disclaimed.

[21] Appl. No.: 2,875

[22] Filed: Jan. 13, 1987

Related U.S. Application Data

[63] Continuation of Ser. No. 610,636, May 16, 1984, abandoned, which is a continuation-in-part of Ser. No. 337,153, Jan. 5, 1982, abandoned, and a continuation-in-part of Ser. No. 455,683, Jan. 5, 1983, abandoned.

[51] Int. Cl.$^5$ ............................................. A01N 43/80
[52] U.S. Cl. .......................................... 71/90; 71/79; 47/57.6
[58] Field of Search ................................................. 71/90

[56] References Cited

U.S. PATENT DOCUMENTS

| | | | |
|---|---|---|---|
| 3,341,547 | 9/1967 | Mailey | 260/302 |
| 3,393,992 | 1/1968 | Mailey | 71/90 |
| 4,380,465 | 4/1983 | Howe et al. | 71/90 |
| 4,459,152 | 7/1984 | Fankhauser et al. | 71/88 |

FOREIGN PATENT DOCUMENTS

| | | |
|---|---|---|
| 0002859 | 4/1979 | European Pat. Off. |
| 2641295 | 3/1977 | Fed. Rep. of Germany |
| 7116163 | 5/1972 | Netherlands |

OTHER PUBLICATIONS

Olvey et al., Proceedings of the Belt-Wide Cotton Conference (1981) p. 8H.

"Chemically Induced Male Sterility, a New Tool in Plant Breeding", F. Wit., *Euphytica*, vol. 9, No. 1, pp. 1 et seq. (1960).

"Evaluation of Certain Chemicals as Selective Gametocides for Wheat", Porter et al., *Crop Science*, pp. 381 et seq. (1961).

"Effects of Sodiium 2,3-dichloroisobutyrate on Six Characteristics of American Upland Cotton", Richmond, *Crop Science*, p. 58 (1961).

"Termination of Late Season Cotton Fruiting with Plant Growth Regulators", Kittock et al., *Crop Science*, vol. 17, No. 7, pp. 320-324 (1977).

Olvey et al., pre-conference brochure of the 1981 Belt-wide Cotton Production Research Conf. & Special Meetings, p. 9, 1981.

Pennwalt Technical Data Sheet for TD-1123, May 15, 1978.

Shaver et al., "Fate of Potassium etc.", (1979), J. Ag. Food Chem. 27, pp. 325-328.

Cathy, "Evaluation of Potassium, etc.", (1978), CA 89 No. 101697a (1978).

"Growth and Development of the Cotton Plant in Arizona", Dennis et al., U. of Arizona pamphlet 8168 (1981).

Kittock et al., "Timing Late-Season Fruiting, etc.," CA 93: 108841; 1980.

"Effect of growth-stimulant acids on the economic characters of intraspecific hybrids of cotton":, Vopr. Genet., selektsii i semenovodstva khlopchatnika i lyutserny, 13, Eshankhodshaev, T., Publ: Tashkent, Uzbek SSR, 1976, 130-135 (in Russian).

"Practical Works with the Selection and Seed-Forming of Agricultural Plants", Moscow, Kolos publishers, 1976, pp. 131 et seq.; Praktikum po seletsii i senenouodstun polevykl Kultur, mokva, kolos, 1976, s. 131.

*Primary Examiner*—Glennon H. Hollrah
*Assistant Examiner*—John D. Pak
*Attorney, Agent, or Firm*—Woodcock Washburn Kurtz Mackiewicz & Norris

[57] ABSTRACT

Cotton plants may be rendered male sterile while retaining substantial female fertility by contracting the plants with a gametocidally effective amount of a novel compound which has the formula:

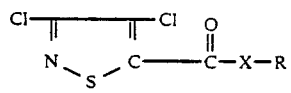

where X is oxygen, sulfur, or

and where R is a substituted and unsubstituted aryl, alkyl, cycloalkyl, alkoxy and alkene group, and maintaining the effective amount for a sufficient time to form sterile plant flowers that can then be pollinated by a second variety cotton plant to provide cotton having hybrid cotton seeds.
30 Claims, 2 Drawing Sheets

METHOD OF HYBRIDIZING COTTON

This is a continuation of application Ser. No. 610,636, filed May 16, 1984, abandoned, which is a continuation-in-part of application Ser. No. 337,153, filed Jan. 5, 1982, abandoned, and also a continuation-in-part of application Ser. No. 455,683, filed Jan. 5, 1983, abandoned.

BACKGROUND OF THE INVENTION

Chemically induced male sterilization using gametocides has been employed in some plant families to effect hybridization. Thus, rows or groups of plants are selected to become the female plants for the production of hybrid seeds. These female plants are rendered male sterile by contact with a selective chemical sterilant or gametocidal compounds. Such rows or groups are interposed with rows or groups of plants selected to perform as male donor plants. Such male donors are not contacted with the gametocide and produce pollen in the normal fashion. This pollen is allowed to contact the female sexual organs of the male sterile female hosts either through wind pollination, hand pollination or through the mediation of insects. If the female hosts are effectively male sterile, self-pollination of such hosts is precluded and uniform, exclusive pollination of such female hosts by the selected male donor plants is ensured. The seeds resulting from such cross-pollination are hybrid in nature and reflect differing male and female parental heritage. Such seeds, when planted and nurtured during subsequent growing cycles, may exhibit hybrid vigor, improved physical traits, and other benefits known to be associated with such hybrid genetics. The publication, "Chemically Induced Male Sterility, a New Tool in Plant Breeding?" F. Wit. *Euphytica* Vol. 9, No. 1 p. 1 et. seq. and "Evaluation of Certain Chemicals as Selective Gametocides for Wheat", Porter et al. *Crop Science* p. 381 et. seq. (1961), provides further background information on this method of growing hybrid seeds.

A plant growth regulator, the potassium salt of 3,4-dichloro-5-isothiazolecarboxylic acid, has been suggested as a selective male gametocide for cotton. See, for example, Olvey et al. pre-conference brochure of the 1981 Betlwide Cotton Production Research Conferences and Special Meetings, p. 9. and U.S. Pat. No. 3,341,547 (as to growth regulating activity generally). No method for attaining effective male sterility in cotton while maintaining good female fertility is known to have been disclosed heretofore, however. Furthermore, no effective gametocidal compositions for the hybridization of cotton are believed to be known.

SUMMARY OF THE INVENTION

The method of this invention is defined as a method of hybridizing a first variety cotton plant with a second variety cotton plant to provide hybrid cotton seeds, comprising:

(a) contacting said first variety cotton plant prior to formation of first plant flowers that are to mature to provide hybrid cotton seeds with a male sterilizing effective amount of an isothiazole compound, that is less than a female sterilizing amount of compound, said compound having the formula:

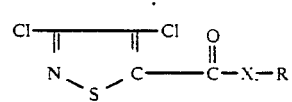

where X is oxygen, sulfur or

provided that when:

(i) X is oxygen R is: naphthyl; phenyl; phenyl substituted with 1 to 2 halogens, halomethyl, 1 to 2 lower alkyl groups of 1 to 4 carbon atoms, 1 to 2 lower alkyl groups of 1 to 4 carbon atoms substituted with fluoro, 1 to 2 methoxy alkyl groups of 1 to 4 carbon atoms, 1 to 2 methoxy alkyl groups of 1 to 4 carbon atoms substituted with fluoro, 1 to 2 nitro groups or trifluoro; ethoxyphenyl; ethoxyphenyl substituted with chloro or methoxy; ethyl thiophenyl; ethyl thiophenyl substituted with chloro or methoxy; a polyethylene glycol bis where the number of ethylene oxide units is from 3 to 6; cyclohexyl; cyclohexyl monosubstituted with a lower alkyl group of 1 to 4carbon atoms; or an alkylene group of 2 to 4carbon atoms;

(ii) X is

R is: phenyl; phenyl substituted with 1 to 2 nitro groups; or a pyridyl group; and (iii) X is sulfur, R is an alkylthioalkyl group in which each alkyl is of 1 to 4 carbon atoms;

(b) maintaining said male sterilizing effective amount in (a) in contact with said first plant throughout a period of the growing season of the first plant sufficient in duration to provide male sterile plant flowers; and (c) exposing said male sterile plant flowers during a period of flower fertility to pollen from said second variety cotton plant to provide pollinated first plant flowers, said pollinated flowers then maturing during the remainder of the growing season to provide cotton having hybrid cotton seeds.

The preferred effective amount of compound is from about 0.1 to about 2.0 pounds per acre. It is preferred to begin applications of the compound at least 14 days prior to formation of first plant flowers and to maintain an effective amount of compound at least until about 12 weeks prior to harvest of the hybrid cotton seeds. It is preferred that the effective amount of the compound in (a) and (b) be sufficient to burn at least a portion of the fingers of the first plant bracts to an extent that does not exceed substantially beyond the inter-finger spaces of the bracts.

A preferred method for so maintaining the effective amount of compound is the process wherein the extent of the bract finger burning is monitored and additional compound is applied to said first plant in response to insufficient bract burning and in response to excessive bract burning said first plant is irrigated with water to maintain said bract burning at a level that does not exceed substantially beyond the inter-finger spaces of the bracts.

The preferred isothiazole compounds for practicing the method of this invention are: Cyclohexyl 3,4- dichloro-5-isothiazolecarboxylic; Phenyl 3,4-dichloro-5-isothiazolecarboxylic; p-Chlorophenyl 3,4-dichloro-5-isothiazolecarboxylic; p-Tolyl 3,4-dichloro-5-isothiazolecarboxylic; p-Anisyl 3,4-dichloro-5-isothiazolecarboxylic; 2-Naphthyl 3,4-dichloro-5-isothiazolecarboxylic; Poly(ethylene glycol)200 bis(3,4-dichloro-5-isothiazolecarboxylic; Poly(ethylene glycol)1000 bis(3,4-dichloro-5-isothiazolecarboxylic); 2,4-Dinitrophenyl 3,4-dichloro-5-isothiazolecarboxylic; 3,4-Dichloro-5-isothiazolecarboxanilide; 4-Methylcyclohexyl 3,4-dichloro-5-isothiazolecarboxylic; 3,3,5-Trimethylcyclohexyl 3,4-dichloro-5-isothiazolecarboxylic; 2-sec-Butyl-4,6-dinitrophenyl 3,4-dichloro-5-isothiazolecarboxylate; 3-Trifluoromethylphenyl 3,4-dichloro-5-isothiazolecarboxylic; 2,6-Dichloro-4(fluorosulfonyl) phenyl 3,4-dichloro-5-isothiazolecarboxylate; S-(3-Propylthio)propyl 3,4-dichloro-5-isothiazolecarbothioate; 3,4-Dichloro-2',4'-dinitro-5-isothiazolecarboxanilide; N-(2-Pyridyl)-3,4-dichloro-5-isothiazolecarboxamide; 4-Chloro-2-fluorosulfonylphenyl 3,4-dichloro-5isothiazolecarboxylate; Allyl 3,4-dichloro-5-isothiazolecarboxylic; 2-(p-Methoxyphenoxy)ethyl 3,4-dichloro-5-isothiazolecarboxylic; 2-(p-Chlorophenylthio)ethyl 3,4-dichloro-5isothiazolecarboxylate; and p-Bromphenyl 3,4-dichloro-5-isothiazolecarboxylate.

The invention also includes hybrid cotton seeds prepared by the above method.

The method of this invention, in its broader scope, is a method for rendering a first variety of cotton plant male sterile, per se, and includes only steps (a) and (b) as above recited.

DETAILED DESCRIPTION OF THE INVENTION

Figure 1:
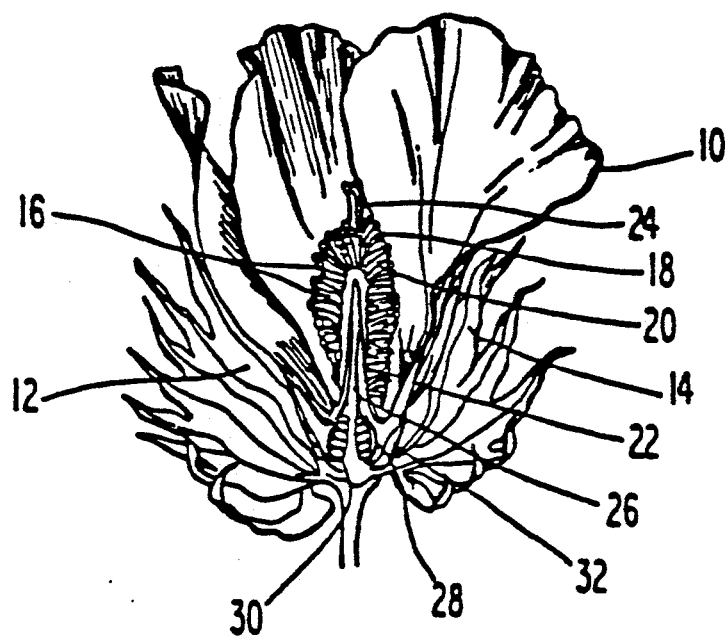
FIG. 1 is a partial cross-sectional rendering of a cotton flower depicting inter alia, the male and female sexual organs and the bracts.

A cotton flower is depicted in FIG. 1. A collection of petals 10 is surrounded by a trio of bracts 12 having a plurality of fingers 14 thereupon. The petals serve to contain and protect the male and female sexual organs of the cotton flower and to attract insect pollination media thereto. Thus, the male sexual organs are represented by pollen-producing stamens 16 each comprising an anther 18 located on a filament 20. Each of the 90 to 100 stamens of the cotton flower is attached to a staminal column 22. The female portion of a cotton flower comprises the pistil composed of the stigma 24, style 26, and ovary 28. The ovary contains a plurality of ovules 30. The cotton flower also comprises a calyx 32 located between the bracts and the petals. The foregoing description has been adapted from "Growth and Development of the Cotton Plant in Arizona," Dennis et. al., U. of Ariz. pamphlet 8168, which is incorporated by reference herein.

Cotton plants may be rendered male sterile while retaining substantial female fertility in accordance with the present invention by contacting the plants with an effective amount of the gametocidal compound, followed by monitoring the degree of burning of the developing bracts of the plant and by adjusting the amount of compound applied to the plants in response to the degree of burning to maintain an effective amount of compound for the appropriate time duration.

Figure 2A:
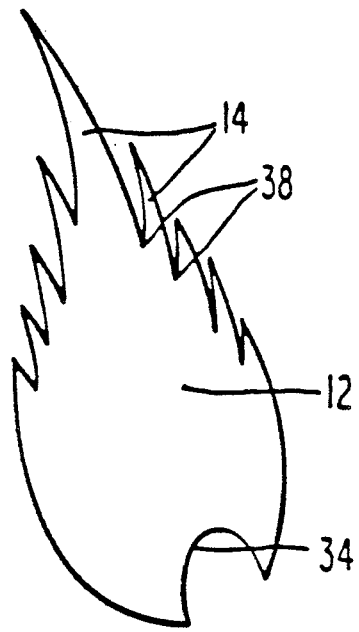
FIG. 2a is a view of a normal cotton flower bract.

FIG. 2a shows a bract in greater detail. Thus, the bract 12 and its fingers 14 are more clearly presented. The inter-finger gaps, 38 are shown. The bract has been removed from the base of the cotton flower at the position indicated by reference number 34. No burning is evidenced in this figure.

Figure 2B:
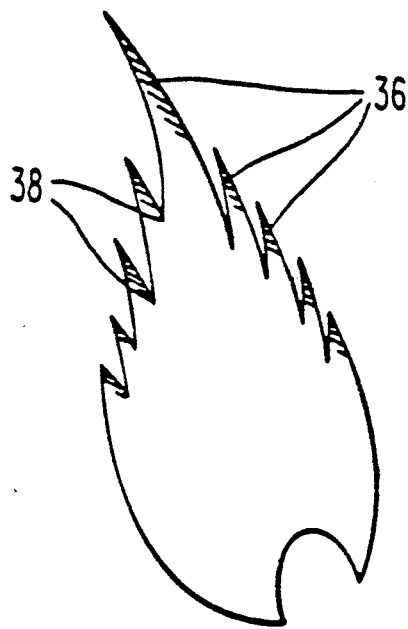
FIG. 2b portrays a cotton bract which has a sensible degree of finger burning.

FIG. 2b portrays a bract exhibiting some finger burning. Thus, crosshatching, 36 indicates areas of browning, wilting or other evidence of phytotoxicity localized on the fingers.

Figure 2C:
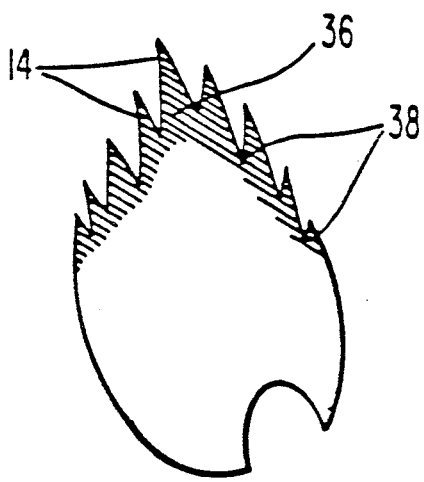
FIG. 2c shows a bract having extensive finger burning which extends somewhat beyond the inter-finger gaps.

FIG. 2c discloses a bract which has undergone extensive finger burning in accordance with the practice of the processes of this invention. Thus, the fingers 14 have been somewhat eroded in size. An area of browning, wrinkling, or other evidence of local phytotoxicity is indicated by crosshatching 36. In this figure, the burning involves most or all of the fingers 14 of the bract and has extended somewhat into the main body portion of the bract beyond the inter-finger gaps, 38 of the bract.

Figure 2D:
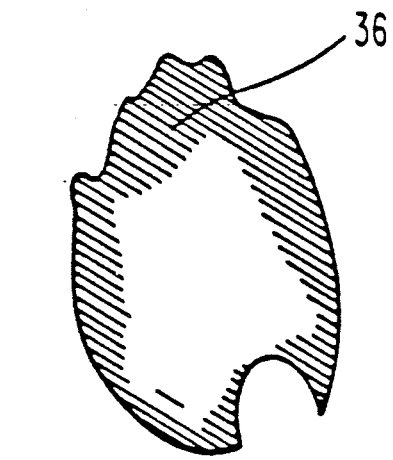
FIG. 2d portrays a cotton bract wherein burning is excessive and has passed beyond finger burning.

FIG. 2d shows an extensively burned bract such as would be the result of an application of an excessive amount of gametocide to a cotton plant. Thus, the fingers have been largely eroded or burned away and an extensive portion of the main bract body beyond the inter-finger gap region has been involved with browning or other evidence of local phytotoxicity, 36. Excessive burning such as depicted in FIG. 2d would be evidence of the application of an excessive amount of gametocide and would imply either loss of reproductive vigor, excessive decline in female fertility, or excessive phytotoxicity generally to the plant.

When sufficient gametocide is applied to cotton plants such that the bracts which subsequently develop on the plant exhibit a sensible degree of "burning" of the finger region—finger burning—then that amount of regulator is sufficient to render the plant male sterile for a period of time. When, however, an amount of gametocide is administered to a cotton plant such the bracts are burned extensively in areas beyond the inter-finger gaps—denominated excessive burning—then such an amount will result in objectionable degrees of female infertility, loss of reproductive vigor, or overall plant phytotoxicity, in addition to rendering the plant male sterile.

When an amount of gametocide is administered to cotton plants which is insufficient to result in effective male sterility of the plants, then the bracts will exhibit substantially no burning.

It will be appreciated that a continuum exists between states of relative non-burning, states of finger burning according to this invention, and states of excessive burning of the bracts of cotton plants treated with gametocide. It is believed that those skilled in the art will have no difficulty, after routine experimentation, in acquainting themselves with that degree of burning which is optimum to provide male sterility without incurring female sterility or other detrimental effects. It will similarly to appreciated that as increasing amount of burning is evidenced on the bracts of cotton plants, that increasing tendencies towards female sterility, loss of reproductive vigor and general phytotoxicity will occur. In general, therefore, finger burning as used in this specification will mean any sensible degree of burning of the fingers of the bracts of a cotton flower which is less than that degree of burning which progresses substantially inwardly of the inter-finger gaps of the bract. That degree of burning depicted in FIG. 2c is intended to represent an approximation of the maximum amount of burning inwardly of the inter-finger gaps, which burning falls within the definition of "finger burning" for most cotton varieties in accordance with this invention. In this regard, however, it will be noted that some burning inwardly of the inter-finger gaps may be exhibited. This burning is far less than the burning exhibited by FIG. 2d wherein substantial involvement inwardly of the inter-finger gaps occurs. It must further be emphasized that finger burning is intended as a qualitative rather than a quantitative term. It is believed that those skilled in the art will have no difficulty in rendering the requirements of finger burning into ordinary practice. It should also be noted that the burning of the bracts need not be symmetric and that an average degree of burning may be employed to determine compliance with the spirit of this invention as described herein.

The active compounds for practicing the invention are as defined in the Summary of the Invention. As these compounds are also novel, the methods of preparation are described in Examples 1 through 23.

The most preferred compounds, because of the ability to provide longer periods of male sterility prior to subsequent application, are Cyclohexyl 3,4-dichloro-5-isothiazolecarboxylate; Phenyl 3,4-dichloro-5-isothiazolecarboxylate; p-Chlorophenyl 3,4-dichloro-5-isothiazolecarboxylate; p-Tolyl 3,4-dichloro-5-isothiazolecarboxylate; p-Anisyl 3,4-dichloro-5-isothiazolecarboxylate; p-Bromphenyl 3,4-dichloro-5-isothiazolecarboxylate; 3-Trifluoromethylphenyl 3,4-dichloro-5-isothiazolecarboxylate; 2-Naphthyl 3,4-dichloro-5-isothiazolecarboxylate; 4-Methylcyclohexyl 3,4-dichloro-5-isothiazolecarboxylate; S-(3-Propylthio)-propyl 3,4-dichloro-5-isothiazolecarboxylate; 2-(p-Methoxyphenoxy)ethyl 3,4-dichloro-5-isothiazolecarboxylate; 2-(p-Chlorophenylthio) ethyl 3,4-dichloro-5-isothiazolecarboxylate; 3,4-dichloro-5-isothiazolecarboxylate; and N-(2-Pyridyl)-3,4-dichloro-5-isothiazolecarboxylate.

These 3,4-dichloro-5 isothiazole carboxylic esters, amides and thioesters are normally either solid or water insoluble liquids which must be formulated into a gametocidal composition for use in the process of this invention. To accomplish this, the gametocidally active ingredient described above is combined with an agriculturally acceptable carrier as exemplified hereinafter. The amount of gametocidally active compound in the composition will range from as little as 1% to as high as 90% active material, prior to any dilution which may be necessary for application to the plants. Preferably, the composition will contain from about 5% to about 20% active ingredient, and most preferably about 10%, although these concentrations are merely for the sake of convenience in applying the gametocidally active constituent in the most efficient and economical manner.

The carrier, which is preferably an aqueous system, will normally include a solvent for the active ingredient and an emulsifier suitable for forming an emulsion of said compound in water. Although the active ingredient may be either solid or liquid, solvents are employed to facilitate dilution of the active ingredient in water for spray application to large areas of land in the aforementioned dosage of about 0.1 to about 2.0 pounds of active ingredient per acre of cotton plants. In a preferred embodiment, the solvent comprises a mixture of a polar solvent and an aromatic solvent. In the experiments described hereinafter, a mixture of equal parts diacetone alcohol and xylene was used as the solvent.

To properly accomplish the formation of an aqueous emulsion of the composition, various emulsifiers are employed which may be used in agricultural applications without adverse effect. Emulsifiers used in the examples described hereinafter are TWEEN ® 20 and TWEEN ® 80, which are well-known commercially available emulsifiers.

As stated above, the amount of active ingredient which is applied to the cotton plants is sufficient such that the bracts which subsequently develop on the plant exhibit a degree of "burning" of the finger region, and at that point, the amount of gametocide is sufficient to render the plant male sterile for a period of time. It should also be noted that the burning of the bracts need not be symmetric and that an average degree of burning may be employed to comply with the spirit of this invention. When, however, an amount of gametocide is administered to a cotton plant such that the bracts are burned extensively in areas beyond the interfinger gaps, then such an amount will result in objectionable degrees of female infertility, loss of reproduction vigor, or overall plant phytotoxicity. In general, therefore, finger burning as used in this specification will mean any sensible degree of burning of the fingers of the bracts of a cotton flower which is less than that degree of burning which progresses substantially inward of the interfinger gaps of the bract. It must further be emphasized that finger burning is intended as a qualitative rather than a quantitative term In the alternativbe, when the amount of gametocide which is administered to the cotton plants is insufficient to result in effective male sterility in the plants, then the bracts will exhibit substantially no burning.

According to the practice of this invention, the amount of gametocidally active material applied to the cotton plants will be monitored in terms of subsequent bract burning and the amount will be altered if necessary, in response to the degree of burning. Preferably, the gametocidally active material may be topically applied such as by a ground level foliar spray or, alternatively it may be applied through irrigation water. Obviously, substantially more material will be required when the compounds are applied through irrigation as opposed to topical sprays. Also, the amount of active material to be applied will vary depending upon the mass of the plants to be treated and, accordingly, with the particular time in the growing season at the time of treatment.

The bracts of the cotton plants should be monitored from three to five days after application of the treatement. In three days, indication of the degree of developing burning of the bracts will be exhibited. In five days, the extent of burning will have been indicated clearly. This process of application followed by monitoring and modification of the amount of application can be practiced throughout the period of time that it is desired that the cotton plants remain male sterile. It has been found that if monitoring of the bracts subsequent to application indicates that an excessive amount has been applied, as evidenced by excessive bract burning, then moderation of the effects of the successive applications may be had such as by application of irrigation water to the plants. It is believed that the usual growth spurt found in cotton which has been irrigated will effectively dilute the concentration of the additive in the plant and cause ti to return to more desirable level as reflected by bract burning monitoring. In general, it will be appreciated, that through a monitoring of a degree of burning of the bracts of cotton flowers, a feedback loop may be obtained whereby the proper amount of gametocidally active material may be established and maintained.

Table I illustrates the effect of application of various compounds of the present invention which were found to provide complete male sterility in cotton plants while producing moderate to slight plant injury and inducing little if any female plant sterility. The various compounds, in an amount ranging from about 5% to about 20%, based on the weight of the solution, were first dissolved in a solvent containing a suitable emulsifier as previously described. The solubilized composition was then formed into an aqueous emulsion and applied to cotton plants in the Southwestern United States on Jul. 1 of the test year by topical spray. One hundred square foot areas of the cotton plants were sprayed in each of the tests listed in Table I. The condition of the plants after spraying was then monitored to determine the number of days after application that bract burning was present in the plants. To effectively maintain male sterility of the plants while retaining the substantial female fertility, additional applications were necessary at the end of the number of days noted for each compound. For example, if plants treated with a given gametocide compound exhibited only thirteen days of 100% male sterility, as evidenced by monitoring the degree of burning of the bracts of the plants, an additional quantity of compound will be required to maintain the male sterility after that thirteen day period of time. Conversely, if the observed sterility was shorter or longer, reapplication of the compound would be necessarily adjusted to comply with the amount of burning of the bracts.

TABLE I

| Compounds of Examples | Active Gametocide Comound | Pounds Active Per Acre | Duration of Male Sterility, Days |
|---|---|---|---|
|  | Control | 0.0 | 0 |
| 2 | Phenyl 3,4-dichloro-5-isothiazolecarboxylate: | 0.72 | 11 |
| 3 | p-Chlorophenyl 3,4-dichloro-5-isothiazolecarboxylate; | 0.64 | 11 |
| 23 | p-Bromophenyl 3,4-dichloro-5-isothiazolecarboxylate | 0.56 | 14 |
| 4 | p-Tolyl 3,4-dichloro-5-isothiazolecarboxylate; | 0.68 | 16 |
| 5 | p-Anisyl 3,4-dichloro-5-isothiazolecarboxylate; | 0.65 | 17 |
| 9 | 2,4-Dintrophenyl 3,4-dichloro-5-isothiazolecarboxylate | 0.65 | 4 |
| 13 | 2-sec-Butyl-4,6-dinitrophenyl 3,4-dichloro-5-isothiazolecarboxylate | 0.65 | 8 |
| 14 | 3,-Trifluoromethylphenyl 3,4-dichloro-5-isothiazolecarboxylate | 0.58 | 11 |
| 15 | 2,6-Dichloro-4-(fluorosulfonyl) phenyl 3,4-dichloro-5-isothiazolecarboxylate | 0.65 | 3 |
| 19 | 4-Chloro-2-fluorosulfonylphenyl 3,4-dichloro-5-isothiazolecarboxylate | 0.65 | 8 |
| 20 | Allyl 3,4-dichloro-5-isothiazolecarboxylate | 0.65 | 3 |
| 21 | 2-(p-Methoxyphenoxy)ethyl 3,4-dichloro-5-isothiazolecarboxylate | 0.57 | 14 |
| 22 | 2-(p-Chlorophenylthio)ethyl 3,4-dichloro-5-isothiazolecarboxylate | 0.54 | 13 |
| 10 | 3,4-Dichloro-5-isothiazolecarboxanilide | 0.72 | 14 |
| 17 | 3,4-Dichloro-2',4'-dinitro-5-isothiazolecarboxanilide | 0.65 | 7 |
| 18 | N-(2-Pyridyl)-3,4-dichloro-5-isothiazolecarboxamide | 0.72 | 15 |
| 1 | Cyclohexyl 3,4-dichloro-5-isothiazolecarboxylate | 0.73 | 13 |
| 11 | 4-Methylcyclohexyl 3,4-dichloro-5-isothiazolecarboxylate | 0.67 | 11 |
| 12 | 3,3,5-Trimethylcyclohexyl 3,4-dichloro-5-isothiazolecarboxylate | 0.65 | 4 |
| 6 | 2-Napthyl 3,4-dichloro-5-isothiazolecarboxylate | 0.70 | 17 |
| 7 | Poly(ethylene glycol)200 bis-(3,4-dichloro-5-isothiazolecarboxylate) | 0.72 | 17 |
| 16 | S-(3-Propylthio)propyl 3,4-dichloro-5-isothiazolecarbothioate | 0.60 | 11 |

The following examples describe the preparation of the novel isothiazole compounds useful in the practice of this invention.

EXAMPLES

Preparation of Novel Compounds

Example 1

Identity: Cyclohexyl 3,4-dichloro-5-isothiazolecarboxylate
Empirical Formula: $C_{10}H_{11}Cl_2NO_2S$;
Mol. Wt.: 280
Equation for Preparation:

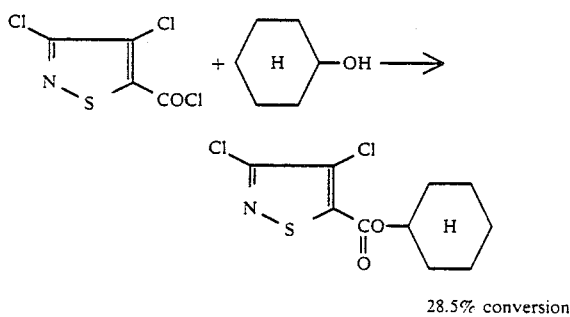

28.5% conversion

Color and Phys. State: Yellow oil
Odor: Indistinct
Ref. Ind.: 1.5443 $D^{25}$
Distn. Range: 80° (0.3) mm.)
Miscellaneous Analyses: Calcd.: C, 43.0%; H, 3.93%; Cl, 25.40%; N, 5.00%. Found: C, 41.83%; H, 3.75%; Cl, 25.50%; N, 5.89%.
Solubility: Water "I" (Insoluble); Diacetone Alcohol: S; Acetone: "S" (Soluble); Xylene: S.
Procedure: To a solution of 21.6 g. (0.1 m) of 3,4-dichloro-5-isothiazolecarboxylate acid chloride in 200 ml. of benzene was added 10.0 g. (0.1 m) of cyclhexanol and the solution was stirred at room temperature for 30 minutes, followed by heating at 50°0 C. for 1 hour. The solution was allowed to stand at room temperature overnight and then concentrated in vacuum. The oil obtained was vacuum distilled to give 8.2 g. (28.5%) of yellow oil, b.p. 80° c. (0.3 mm.), $n_D^{25}$ 1.5443.
Alternate Procedure: To 43.3 g. (0.2 m.) of 3,4-dichloro-5-isothiazolecarboxylate acid chloride and 22.2 g. (0.22 m.) of triethylamine in 250 ml. of toluene was added 20 g. (0.2 m.) of cyclohexanol in 25 ml. of toluene. The resulting slurry was heated to 80° C. for 3 hours, cooled and filtered to remove 28 g. of triethylamine hydrochloride. The filtrate was contrated at 40° C. under reduced pressure and the residue distilled to give 41.7 g. (74.3% conversion) of product, b.p. 139°-140° C. (0.7 mm.); $n_D^{25}$ 1.5444.

Example 2

Identity: Phenyl 3,4-dichloro-5-isothiazolecarboxylate
Empirical Formula: $C_{10}H_5Cl_2NO_2S$
Mol. Wt.: 274
Equation for Preparation:

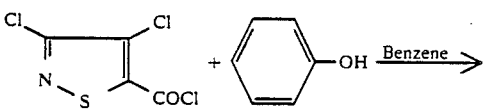

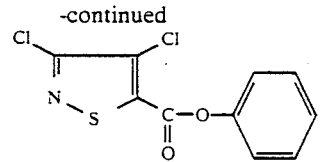

38.5% conversion

Color and Phys. State: White solid
Odor: None
M.P. 61°-63° C.
Miscellaneous analyses: Calcd. C, 44.0%; H, 2.01%; Cl, 25.80%; N, 5.12%. Found: C, 43.81%; H, 1.92%; Cl, 26.11%; N, 5.05%.
Solubility: Water: SS; Diacetone Alcohol: S; Acetone: S; Xylene: S.
Procedure: To a solution of 21.6 g. (0.1 m) of 3,4-dichloro-5-isothiazolecarboxylate acid chloride and 10.0 g. (0.1 m) of triethylamine in 200 ml. of benzene was added 9.4 g. (0.1 m) of warm phenol drops with stirring at room temperature. The mixture was filtered and the filtrate was concentrated in vacuum and refrigerated 65 hours. The dark solid obtained was recrystalized from ethanol to give 7.1 g. (38.5% conversion) of product, m.p. 61°-63° C.

Example 3

Identity: p-Chlorophenyl 3,4-dichloro-5-isothiazolecarboxylate
Empirical Formula: $C_{10}H_4Cl_3NO_2S$;
Mol. Wt.: 308.5
Equation for Preparation:

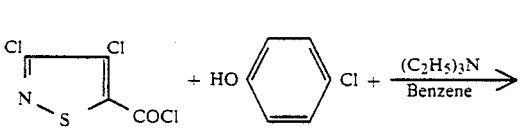

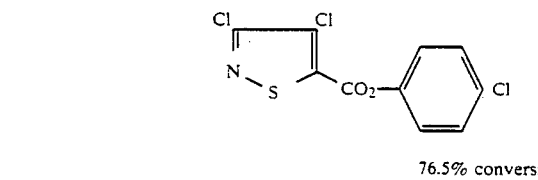

76.5% conversion color and Phys. State: Off-white solid
M.P. 79°-81° C.
Miscellaneous Analyses: Calcd: C, 38.9%; H, 1.30%; Cl, 34.5%; S, 10.37%. Found: C, 38,99%; H, 1.23%; Cl, 34.19%; S, 10.32%.
Solubility: Water: I; Diacetone Alcohol: S; Acetone: S; Xylene; S.
Procedure: To a solution of 11 g. (0.05 m.) of 3,4-dichloro-5-isothiazolecarboxylate acid chloride in 200 ml. of benzene and 5.6 g. (0.055 m.) of triethylamine was added 6.5 g. (0.05 m.) of p-chlorophenol at room temperature. The resulting mixture as stirred at room temperature for 2 hours, and filtered to remove the triethylamine hydrochloride. The solvent was removed from the filtrate in vacuum leaving a tan solid; recrystallization from ethanol (90 ml.) gave 11.8 g. (76% conversion) of product, m.p. 79°-81° C.

Example 4

Identity: p-Tolyl 3,4-dichloro-5-isothiazolecarboxylate
Empirical Formula: $C_{11}H_7Cl_2NO_2S$;

Mol. Wt.: 288
Equation for Preparation:

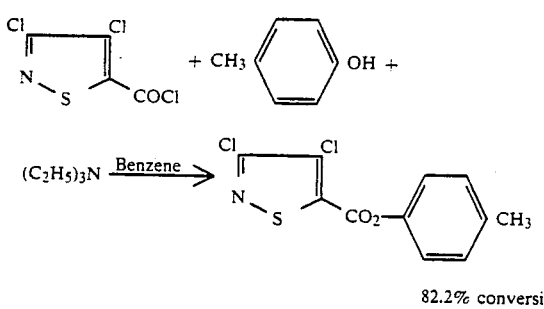

82.2% conversion

Color and Phys. State: White crystalline solid
M.P. 73°–75° C.

Miscellaneous Analyses: Calcd: C, 45.80%; H, 2.43%; Cl, 24.38%; S, 11.11%. Found: C, 45.80%; H, 2.61%; Cl, 24.79%; S, 11.24%.

Solubility: Water: I; Diacetone Alcohol: S; Acetone: S; Xylene: S.

Procedure: To a solution of 11 g. (0.05 m.) of 3,4-dichloro-5-isothiazolecarboxylate acid chloride in 200 ml. of benzene and 5.6 g. (0.055 m.) of triethylamine was added 5.4 g. (0.05 m.) of p-cresol. The resulting slurry was stirred at ambient temperature for 2 hours, filtered to remove triethylamine hydrochloride and the filtrate evaporated in vacuum to leave a tan solid. Recrystallization from ethanol gave 11.9 g. (82.2%) conversion of white solid product, m.p. 73°–75° C.

Example 5

Identity: p-Anisyl 3,4-dichloro-5-isothiazolecarboxylate
Empirical Formula: $C_{11}H_7Cl_2NO_3S$;
Mol. Wt.: 304
Equation for Preparation:

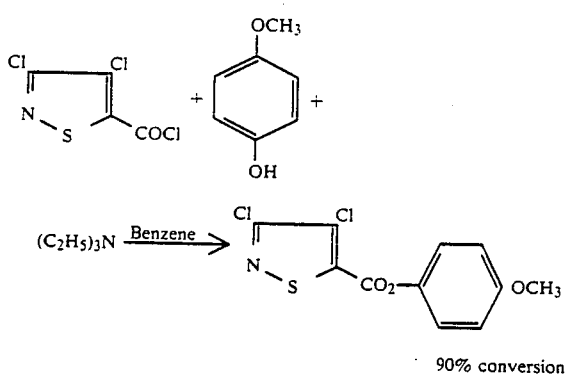

90% conversion

Color and Phys. State: Yellow needles
M.P. 104°–106° C.

Miscellaneous Analyses: Calcd: C, 43.40%; H, 2.30%; Cl, 23.39; S, 10.53%: Found: C, 43.86%; H, 2.77%; Cl, 22.52%; S, 11.01%.

Solubility: Water: I; Diacetone Alcohol: S; Acetone: S; Xylene: S.

Procedure: To a solution of 11.0 g. (0.05 m.) of 3,4-dichloro-5-isothiazolecarboxylate acid chloride in 200 ml. of benzene and 5.6 g. (0.055 m.) of triethylamine was added 6.2 g. of p-methoxyphenol. The resulting slurry was stirred for 2 hours at ambient temperature, filtered to remove triethylamine hydrochloride and the filtrate evaporated in vacuum to leave a brown solid. Recrystallization from ethanol gave 13.7 g. (90.0% conversion) of yellow product, m.p. 104°–106° C.

EXAMPLE 6

Identity: 2-Naphthyl 3,4-dichloro-5-isothiazolecarboxylate
Empirical Formula: $C_{14}H_7Cl_2NO_2S$;
Mol. Wt.: 324
Equation for Preparation:

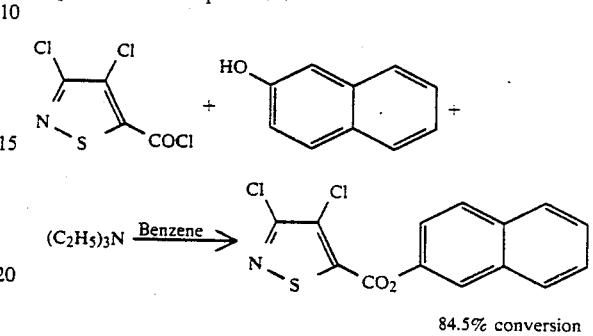

84.5% conversion

Color and Phys. State: White Solid
M.P. 127°–128° C.

Miscellaneous Analyses: Calcd: c, 51.80%; H, 2.16%; Cl, 21.82%; S 9.88%. Found: C, 52.08%; H, 2.57%; Cl, 22.13%; S, 9.71%.

Solubility: Water: I; Diacetone Alcohol: s; Acetone: s; Xylene: s.

Procedure: To a solution of 11 g. (0.05 m.) of 3,4-dichloro-5-isothiazolecarboxylate acid chloride in 200 ml. of benzene and 5.6 g. (0.055 m.) of triethylamine was added 7.2 g. (0.05 m.) of β-naphthol. The resulting slurry was stirred for 2 hours, filtered to remove the amine hydrochloride and the filtrate evaporated in vacuum to leave a brown solid. Recrystallization from ethanol gave 13.7 g. (84.5% conversion) of product, m.p. 127°–128° C.

EXAMPLE 7

Identity: Poly(ethylene glycol)200 bis (3,4-dichloro-5-isothiazolecarboxylate)
Empirical Formula: $C_{16.2}H_{16.5}Cl_4N_2O_{7.1}S_2$;
Mol. Wt.: 560 av.
Equation for Preparation:

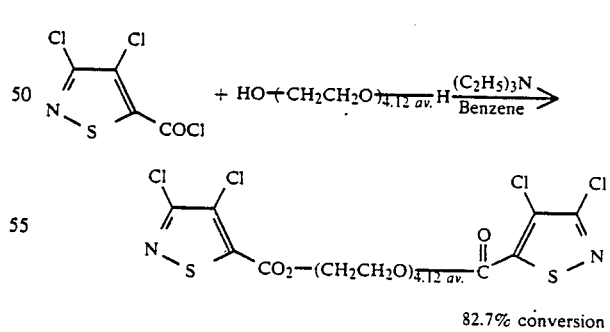

82.7% conversion

Color and Phys. State: Brown oil
Ref. Ind.: $1.5522_D^5$

Miscellaneous Analyses: Calcd: C, 34.9%; H, 2.94%; Cl, 25.38%; S, 11.42%. Found: C, 35.03%; H, 2.99%; Cl, 24.99%; S, 11.52%.

Solubility: Water: I; Diacetone Alcohol: s; Acetone: S; Xylene: S.

Procedure: To a solution of 11 g. (0.05 m.) of 3,4-dichloro-5-isothiazolecarboxylate acid chloride and 5.6 g. (0.55 m.) of triethylamine in 200 ml. of benzene was added a solution of 5 g. (0.025 m.) of poly(ethylene glycol) m.w. 200. The resulting mixture was stirred for 2 hours at ambient temperature and the amine hydrochloride filtered off. The filtrate was washed four times with 25 ml. portions of 10% Na₂CO₃ and four times with 50 ml. portions of water, dried over anhyd. MgSO₄ and filtered. The filtrate was evaporated in vacuum at 50° C. to give 11.6 g. (82.7% conversion) of a dark brown oil, $n^{D25}$1.5520.

EXAMPLE 8

Identity: Poly(ethylene glycol)1000 bis(3,4-dichloro-5-isothiazolecarboxylate)
Empirical Formula: $C_{52.6}H_{89.2}Cl_4N_2O_{25.3}S_2$;
Mol. Wt.: 1360 av.
Equation for Preparation:

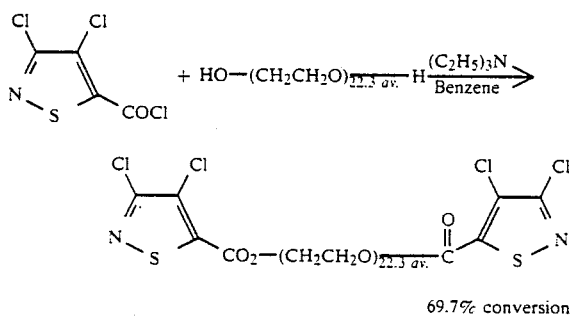

69.7% conversion

Color and Phys. State: Brown oil
Ref. Ind.: 1.5004 D²⁵

Miscellaneous Analyses: Calcd: C, 46.4%; H, 6.57%; Cl, 10.43%; S, 4.71%. Found: C, 45.59%, H, 6.47%; Cl, 11.18%; S, 6.00%.

Solubility: Water: I; Diacetone Alcohol: S; Acetone: S; Xylene: S.

Procedure: To a solution of 11 g. (0.05 m.) of 3,4-dichloro-5-isothiazolecarboxylate acid chloride and 5.6 g. (0.055 m.) of triethylamine in 200 ml. of benzene was added a solution of 25 g. (0.025 m.) of poly(ethylene glycol) m.w. 1000 in 25 ml. of benzene. The resulting slurry was stirred at ambient temperature for 2 hours and the amine hydrochloride filtered off. The filtrate was washed three times with 25 ml. portions of 10% HCl, three times with 25 ml. portions of 10% Na₂CO₃, and three times with 50 ml. portions of H₂O, dried over anhyd. MgSO₄ and filtered. The filtrate was evaporated in vacuum at 50° C. to give 23.7 g. (69.7% conversion) of a brown oil, $n^{D25}$1.5004.

Example 9

Identity: 2,4-Dinitrophenyl 3,4-dichloro-5-isothiazolecarboxylate
Empirical Formula: $C_{10}H_3Cl_2N_3O_6S$;
Mol. Wt.: 364
Equation for Preparation:

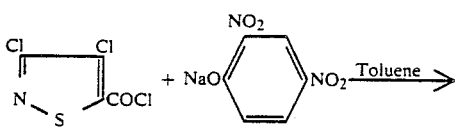

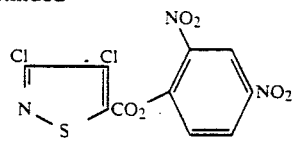

34.1% conversion

Color and Phys. State: Off-white solid
M.P. 109°–110° C.

Miscellaneous Analyses: Calcd: C, 33.00%; H, 0.83%; S, 8.80%. Found: C, 33.52%; H, 1.39%; S, 8.83%.

Solubility: Water: I; Diacetone Alcohol: S; Acetone: s; Xylene: S.

Procedure: To 10 g. (0.05 m.) of the sodium salt of 2,4-dinitrophenol in 125 ml. of toluene was added 11 g. (0.05 m) of 3,4-dichloro-5-isothiazolecarboxylate acid chloride. The resulting slurry was heated at 80° C. for 24 hours, cooled and filtered. The filtrate was concentrated in vacuum and the brown oil treated with ether to give 6.6 g. of product, m.p. 104°–107° C. Recrystallization from acetone-petroleum ether gave 6.2 g. (34.1% conversion), m.p. 109°–110° C.

Example 10

Identity: 3,4-dichloro-5-isothiazolecarboxylate
Empirical Formula: $C_{10}H_6Cl_2N_2OS$;
Mol. Wt.: 273
Equation for Preparation:

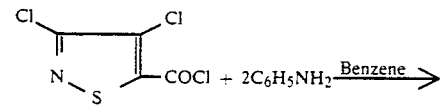

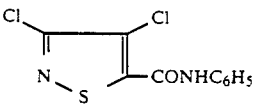

91% conversion

Color and Phys. State: White solid
Odor: None
M.P. 123°–124° C.

Miscellaneous Analyses: Calcd: C, 44.0%; H, 2.2%; Cl, 26.04%. Found: C, 43.96%; H, 2.33%; Cl, 25.85%.

Solubility: Water: I; Diacetone Alcohol: S; Acetone: S; Xylene: S.

Procedure: To a solution of 6.5 g. (0.03 m) of 3,4-dichloro-5-isothiazolecarboxylate acid chloride in 150 ml. of benzene was added 5.6 g. (0.06 m) of aniline in 30 ml. of benzene in 5 min. The reaction mixture was stirred for 7 hours and left standing overnight. The solvent was evaporated under reduced pressure and 50 ml. of water was added to residue. The reaction mixture was extracted with 250 ml. of chloroform an the chloroform extract was washed (H₂O) and dried (MgSO₄). Evaporation of the solvent gave 7.5 g. (91%) of white solid, m.p. 122°–124° C. A 0.6 g. portion was recrystallized from 30 ml. of chloroform and 10 ml. of hexane to give product of m.p. 123°–124° C.

Example 11

Identity: 4-Methylcyclohexyl 3,4-dichloro-5-isothiazolecarboxylate

Empirical Formula: $C_{11}H_{13}Cl_2NO_2S$;
Mol. Wt.: 294
Equation for Preparation:

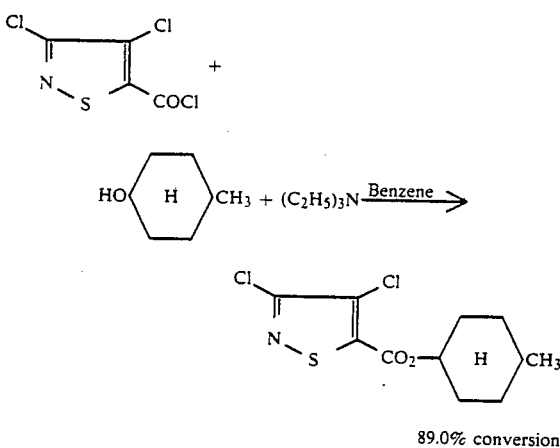

89.0% conversion

Color and Phys. State: Yellow oil
Odor: None
Ref. Ind.: 1.5330 $D^{25}$

Miscellaneous Analyses: Calcd: C, 45.0%; H, 4.45%; S, 10.90%. Found: C, 44.89%; H, 4.63%; S, 10.63%.

Solubility: Water: I; Diacetone Alcohol: S; Acetone: S; Xylene: S.

Procedure: A mixture of 5.5 g. (0.02 m.) of 3,4-dichloro-5-isothiazolecarboxylate acid chloride, 2.8 g. (0.025 m.) of 4-methylcyclohexanol and 2.5 g. of triethylamine in 100 ml. of benzene was stirred at room temperature for 2 hours and then heated on the steam bath for 2 hours. The mixture was allowed to remain at room temperature overnight, filtered and the filtrate concentrated in vacuum to obtain 6.6 g. (89.0% conversion) of yellow oil, $n_D^{25}$ 1.5330. The product could not be distilled at 180° (1.0 m.m) head temperature.

Example 12

Identity: 3,3,5-Trimethylcyclohexyl 3,4-dichloro-5-isothiazolecarboxylate.
Empirical Formula: $C_{13}H_{17}Cl_2NO_2S$;
Mol. Wt.: 322
Equation for Preparation:

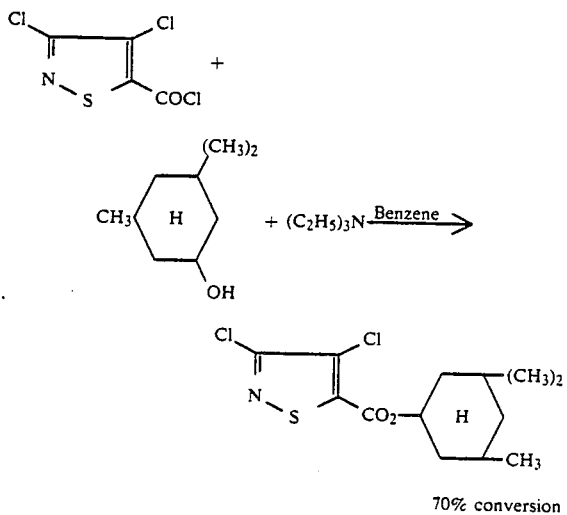

70% conversion

Color and Phys. State: Brown oil

Ref. Ind.: 1.5255 $D^{25}$

Miscellaneous Analyses: Calcd: C, 48.5%; H, 5.3%; Cl, 22.1%. Found: C, 48.88%; H, 5.58%; Cl, 22.19%.

Solubility: Water: I; Diacetone Alcohol: S; Acetone: S; Xylene: S.

Procedure: To 11.0 g. (0.05 m) of 3,4-dichloro-5-isothiazolecarboxylate acid chloride, 5.0 g. (0.05 m.) of triethylamine in 100 ml. of benzene was added 7.1 g. (0.05 m.) of 3,3,5-trimethyl-cyclohexanol. The mixture was stirred at room temperature for 2 and on a steam bath for 2 hours, then filtered. The filtrate was concentrated in vacuum to obtain 11.2 g. (70% conversion) brown oil which could not be distilled, at head temperature of 172° C. (0.8 mm.); $n_D^{25}$ 1.5255.

Example 13

Identity: 2-sec-Butyl-4,6-dinitrophenyl 3,4-dichloro-5-isothiazolecarboxylate
Empirical Formula: $C_{14}H_{11}Cl_2N_3O_6S$;
Mol. Wt.: 420
Equation for Preparation:

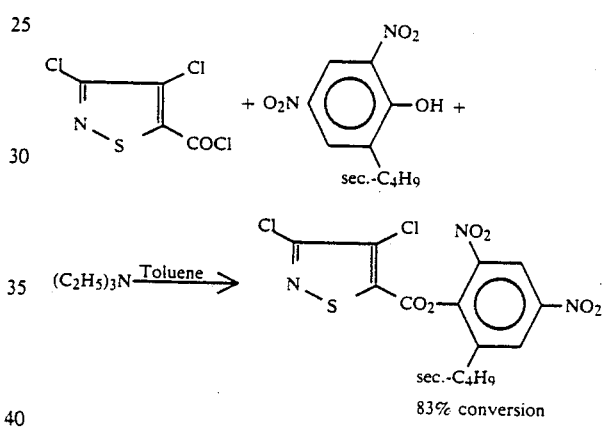

83% conversion

Color and Phys. State: White solid
Odor: None
M.P. 85°–86° C.

Miscellaneous Analyses: Calcd: C, 40.0%; H, 2.62%; S, 7.60%. Found: C, 39.81%; H, 3.02%; S, 7.74%.

Solubility: Water: I; Diacetone Alcohol: S; Acetone: S; Xylene: S.

Procedure: To 11.0 g. (0.05 m.) of 3,4-dichloro-5-isothiazolecarboxylate acid chloride, and 5.0 g. (0.05 m.) of triethylamine in 100 ml. of toluene was added 12.0 g. (0.05 m.) of 2-sec-butyl-4,6-dinitrophenol (distilled). The reaction mixture was heated on a steam bath for 4 hours and filtered. The filtrate was concentrated in vacuum to obtain a brown oil which, on standing overnight, showed the presence of solid. The reaction product was then treated with 95% ethanol and filtered to give 17.4 g. (83% conversion) of solid which was recrystallized from hexane to give product, m.p. 85°–86° C.

Example 14

Identity: 3-Trifluoromethylphenyl 3,4-dichloro-5-isothiazolecarboxylate.
Empirical Formula: $C_{11}H_4Cl_2F_3NO_2S$;
Mol. Wt.: 342
Equation for Preparation:

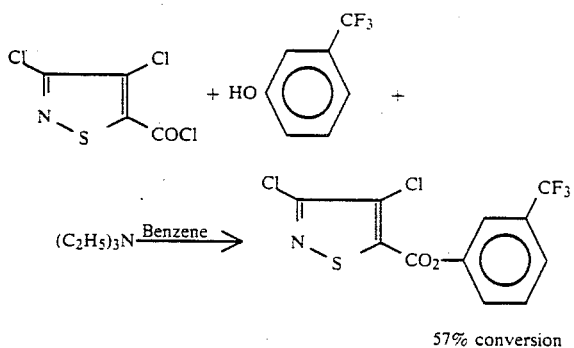

57% conversion

Color and Phys. State: Yellow solid
Distn. Range: 180° (1.5 mm.)
M.P. 53°–56° C.

Miscellaneous Analyses: Calcd: C, 38.7%; H, 1.17%; S, 9.35%. Found: C, 39.21%; H, 1.46%; S, 9.51%.

Solubility: Water: I; Diacetone Alcohol: S; Acetone: S; Xylene: S.

Procedure: A mixture of 11.0 g. (0.05 m.) of 3,4-dichloro-5-isothiazolecarboxylate acid chloride, 5.0 g. of triethylamine, and 8.1 g. (0.05 m.) of m-trifluoromethylphenol in 100 ml. of benzene was stirred at room temperature for 2 hours, and then heated on a steam bath for 2 hours. The mixture was filtered and the filtrate concentrated in vacuum to obtain a dark brown oil which was vacuum distilled to give 9.8 g. (57% conversion) of product, b.p. 180° C. (1.5 mm.) The product solidified on cooling, m.p. 53°–56° C.

Example 15

Identity: 2,6-Dichloro-4-(fluorosulfonyl)phenyl 3,4-dichloro-5-isothiazolecarboxylate
Empirical Formula: $C_{10}H_2Cl_4FNO_4S_2$; Mol. Wt.: 425
Equation for Preparation:

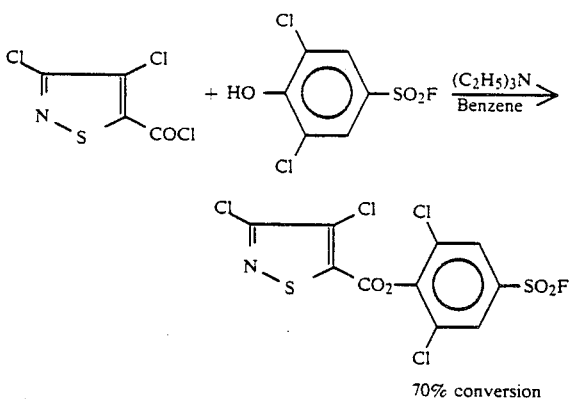

70% conversion

Color and Phys. State: Pale yellow solid
Odor: None
M.P. 130°–131° C.

Miscellaneous Analyses: Calcd: C, 28.3%; H, 0.47%; Cl, 33.5%. Found: C, 28.66%; H, 0.87%; Cl, 33.85%.

solubility: Water: I; Diacetone Alcohol: S; Acetone: S; Xylene: S.

Procedure: To a mixture of 8.7 g. (0.05 m.) of 3,4-dichloro-5-isothiazolecarboxylate acid chloride and 4.0 g. of triethylamine in 100 ml. of benzene was added 9.8 g. (0.04 m.) of 2,6-dichloro-4-(fluorosulfonyl)phenol and the mixture stirred at room temperature for 2 hours and on the steam bath for 2 hours. The mixture was filtered and the filtrate concentrated in vacuum to obtain a solid which was recrystallized from ether-petroleum ether to give 11.9 g. (70% conversion) of product, m.p. 130°–131°C.

Example 16

Identity: S-(3-Propylthio)propyl 3,4-dichloro-5-isothiazolecarboxylate
Empirical Formula: $C_{10}H_{13}Cl_2NOS_3$;
Mol. Wt.: 330
Equation for Preparation:

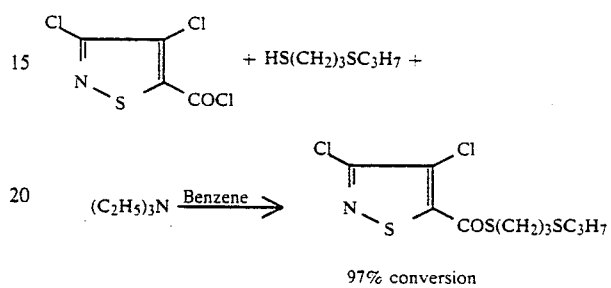

97% conversion

Color and Phys. State: Dark brown oil
Odor: Stench
Ref.Ind.: 1.5805 $D^{25}$
Distn. Range: Decomposes Miscellaneous Analyses: Calcd: C, 36.50%; H, 3.95%; Cl, 21.5%; S, 29.0%. Found: C, 37.67%; H, 4.53%; Cl, 19.86%; S, 28.52%.

Solubility: Water: I; Diacetone Alcohol: S; Acetone: S; Xylene: S.

Procedure: To 11.0 g. (0.05 mole) of 3,4-dichloro-5-isothiazolecarboxylate acid chloride and 5.0 g. (0.05 m) of triethylamine in 150 ml. of benzene was added 7.5 g. (0.05 m) of (3-propylthio)propanethiol. The mixture was refluxed for 6 hours, and allowed to stand at room temperature over the weekend. The mixture was filterd and the filtrate concentrated in vacuum to obtain 16.0 g. (97% conversion) of dark brown oil, $nD^{25}$ 1.5805. The product decomposed on attempted distillation and analysis was obtained on the undistilled material.

Example 17

Identity: 3,4-Dichloro-2',4'-dinitro-5-isothiazolecarboxanilide
Empirical Formula: $C_{10}H_4Cl_2N_4O_5S$;
Mol. Wt.: 363
Equation for Preparation:

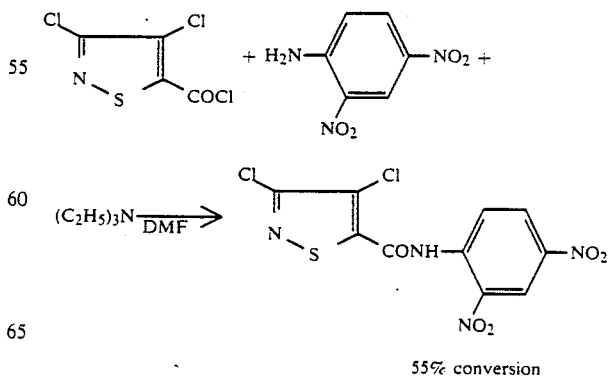

55% conversion

Color and Phys. State: Tan solid

Odor: None
M.P. 154°-155° C.
Miscellaneous Analyses: Calcd: C, 33.05% H, 1.18%; Cl, 19.58%. Found: C, 32.68%; H, 1.27%; Cl, 19.62%.
Solubility: Water: I; Diacetone Alcohol: SS; Acetone: S; DMF: S.
Procedure: A solution of 3.9 g. (10 m mole) of 3,4-dichloro-5-isothiazolecarboxylate acid chloride and 2.75 g. (15 m mole) of 2,4-dinitroaniline in 50 ml. of DMF was stirred at room temperature overnight. A solid appeared which was collected and air-dried to give 0.55 g. of a yellow powder, m.p. 231°-233° C. which was not characterized. The filtrate was returned to the reaction pot and stirred for several days with no visible change occurring; 1.8 g. of triethylamine was then added and a solid immediately formed. After stirring at room temperature for 6 hours, the triethylamine hydrochloride was filtered off and the filtrate was poured into 400 ml. of water. The resulting solid was collected; washed with water and air-dried to give 3.8 g. of pale yellow solid, m.p. 122°-132° C. The solid was immediately dissolved in ca 75 ml of acetone and precipitated with water. There resulted 3.0 g. (50% conversion) of tan solid, m.p. 154°-155° C. An analytical sample was prepared by recrystallization from acetone, m.p. 154°-155° C.

Example 18

Identity: N-(2-Pyridyl)-3,4-dichloro-5-isothiazolecarboxamide
Empirical Formula: $C_9H_5Cl_2N_3OS$; Mol. Wt.: 274
Equation for Preparation:

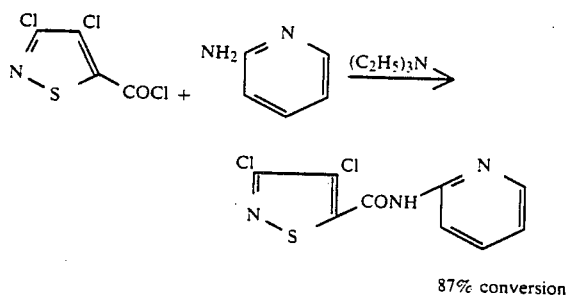

87% conversion

Color and Phys. State: Light violet solid
Odor: None
M.P. 109°-111° C. Miscellaneous Analyses: Calcd: C, 39.43%; H, 1.84%; S, 11.69%. Found: C, 38.64%; H, 2.06%; S, 12.10%.
Solubility: Water: I; Diacetone Alcohol: S; Acetone: S; DMF: S.
Procedure: To a solution of 64.8 g. (0.3 m) of 3,4-dichloro-5-isothiazolecarboxylate acid chloride in 250 ml. of benzene was added simultaneously (using two additional funnels) 30 grams (0.3 m) of triethylamine and a solution of 28 g. (0.3 m) of 2-aminopyridine in 100 ml. of benzene. The solution was stirred vigorously during the addition and the temperature was maintained between 25°-30° C. After the addition, the mixture was set aside at room temperature for 6 hours. The amine hydrochloride was filtered off and the residue washed with 100 ml. of hot benzene. The filtrate was then washed thoroughly with water, dried over $Mg_2SO_4$, and concentrated in vacuo to give the solid which was recrystallized from benzene to get 70 g. (87% conversion) of product, m.p. 109°-111° C.

Example 19

Identity: 4-Chloro-2-fluorosulfonylphenyl 3,4-dichloro-5-isothiazolecarboxylate.
Empirical Formula: $C_{10}H_3Cl_3FNO_4S_2$;
Mol. Wt.: 390.5
Equation for Preparation:

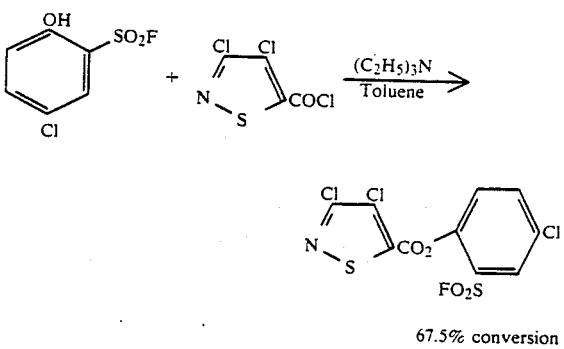

67.5% conversion

Color and Phys. State: Off-white solid
Odor: None
M.P. 110°-111° C.
Miscellaneous analyses: Found: C, 31.23%; H, 1.07%; N, 4.58%. Calcd: C, 30.74%; H, 0.76%; N, 4.85%.
Solubility: Water: I; Diacetone Alcohol: S; Acetone: S; DMF: S.
Procedure: To a stirring solution of 8.4 g. (0.04 m) of 3-chloro-5-hydroxybenzene sulfonyl fluoride, 4.2 g. (0.04 m) of triethylamine, and 100 ml. of toluene, was added 8.7 g. (0.04 mole) of 3,4-dichloro-5-isothiazolecarboxylate acid chloride in 10 ml. of toluene. After the slight exotherm had abated, the reaction was stirred 1½ hours, at reflux, cooled and filtered. The triethylamine hydrochloride cake was washed with a little toluene, and the filtrate was evaporated in vacuum to give a residue of 16 g. of light tan solid, m.p. 106°-109° C. This residue was treated with a boiling mixture of petroleum ether and toluene, filtered hot to remove a small amount of insoluble material, and the filtrate chilled to obtain 10.5 g. (67.5% conversion) of off-white solid, m.p. 109°-111° C. An analytical sample was recrystallized twice more, m.p. 110°-111° C.

Example 20

Identity: Allyl 3,4-dichloro-5-isothiazolecarboxylate
Empirical Formula: $C_7H_5Cl_2NO_2S$;
Mol. Wt.: 238
Equation for Preparation:

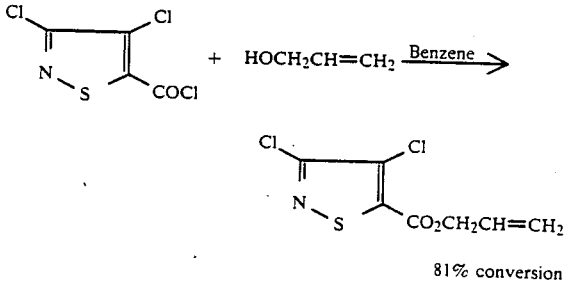

81% conversion

Color and Phys. State: Brown liquid and solid
Ref.Ind.: 1.5510 $D^{25}$
Miscellaneous Analyses: Calcd: C, 35.4%; H, 2.1%; S, 13.4%. Found: C, 35.93%; H, 2.58%; S, Solubility: Water: I; Diacetone Alcohol: S; Acetone: S; DMF: S.

Procedure: To a mixture of 10.8 g. (0.05 m) of 3,4-dichloro-5-isothiazolecarboxylic acid chloride and 5.0 g (0.05 m) of triethylamine in 150 ml of benzene at room temperature was added 3.0 g. (0.5 m) of allyl alcohol. The mixture was stirred at room temperature for 3 hours, on a steam bath for 1 hour, cooled and filtered. The filtrate was concentrated in vacuum to give 9.6 g (81% conversion) of brown oil.

EXAMPLE 21

Identity: 2-(p-Methoxyphenoxy)ethyl 3,4-dichloro-5-isothiazolecarboxylate
Empirical Formula: $C_{13}H_{11}Cl_2NO_4S$;
Mol. Wt.: 348
Equation for Preparation:

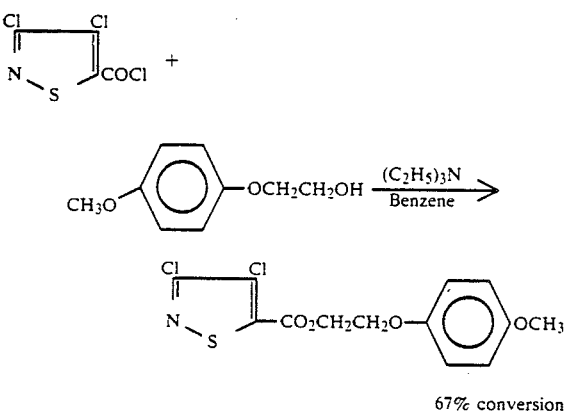

67% conversion

Color and Phys. State: Yellow solid
M.P. 62°-64° C.

Miscellaneous Analyses: Calcd: C, 44.8%; H, 3.16%; S, 9.2%. Found: C, 44.95%; H, 3.28%; S, 9.36%.

Solubility: Water: I; Diacetone Alcohol: S; Acetone: S; DMF: S.

Procedure: A mixture of 5.5 g. (0.025 m) of 3,4-dichloro-5-isothiazolecarboxylic acid chloride, 4.2 g. (0.025 m) of 2-(4-methoxyphenoxy)ethanol and 2.5 g. (0.025 m) of triethylamine in 150 ml. of benzene was heated on a steam bath for 6 hours, and filtered hot. The filtrate was concentrated in vacuum to give an oil which crystallized within 24 hours at room temperature. The solid was recrystallized from ethanol to give 5.8 g. (67% conversion) of product, m.p. 62°-64° C.

EXAMPLE 22

Identity: 2-(p-Chlorophenylthio)ethyl 3,4-dichloro-5-isothiazolecarboxylate
Empirical Formula: $C_{12}H_8Cl_3NO_2S_2$;
Mol. Wt.: 368.5
Equation for Preparation:

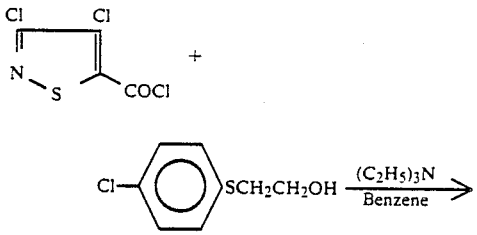

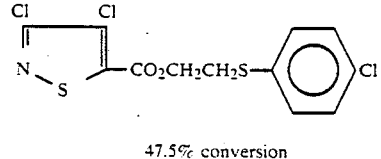

47.5% conversion

Color and Phys. State: White solid
Odor: None
M.P. 58°-60° C.

Miscellaneous Analyses: Calcd: C, 39.0%; H, 2.17%; S, 17.4%. Found: C, 39.15%; H, 2.45%; S, 17.21%.

Solubility: Water: I; Diacetone Alcohol: S; Acetone: S; DMF: S.

Procedure: A mixture of 11.0 g. (0.05 m) of 3,4-dichloro-5-isothiazolecarboxylic acid chloride, 9.5 g. (0.05 m) of 2-(4-chlorophenyl)thioethanol and 5.0 g (0.05 m) of triethylamine in 150 ml. of benzene was heated on a steam bath for 4 hours and filtered hot. The filtrate was concentrated in vacuum to give an oil which solidified on standing at room temperature for 24 hours. The solid was recrystallized from ethanol to give 8.9 g. (47.5% conversion) of product, m.p. 58°-60° C.

EXAMPLE 23

Identity: p-Bromphenyl 3,4-dichloro-5-isothiazolecarboxylate
Empirical Formula: $C_{10}H_4BrCl_2NO_2S$;
Mol. Wt.: 353
Equation for Preparation:

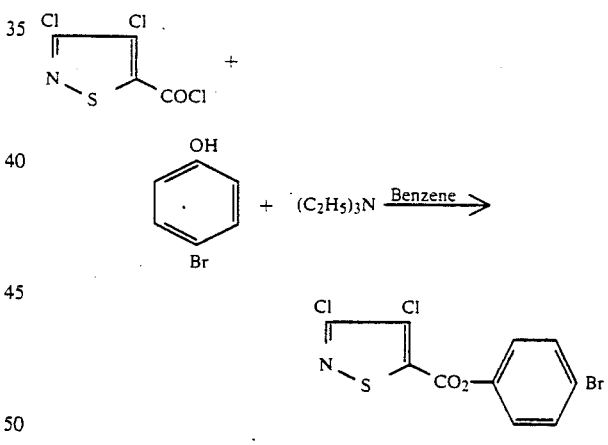

91% conversion

Color and Phys. State: White solid
M.P. 94°-96° C.

Miscellaneous Analyses: Calcd: C, 34.05% H, 1.13%; Br, 22.68%; S, 9.06% Found: C, 34.09%; H, 1.40%; Br, 23.06%; S, 9.00%.

Solubility: Water: I; Diacetone Alcohol: S; Acetone: S; Xylene: S.

Procedure: To a solution of 11 g. (0.05 m.) of 3,4-dichloro-5-isothiazolecarboxylic acid chloride in 200 ml. of benzene and 5.6 g. (0.055 m.) of triethylamine was added 8.7 g. (0.05 m.) of p-bromophenol in 25 ml. of benzene. The resulting slurry was stirred at ambient temperature for 2 hours, filtered to remove amine hydrochloride; and the filtrate evaporated in vacuum. The solid residue was recrystallized from ethanol to give 16.1 g. (91% conversion) of a white product, m.p. 94°-96° C.

We claim:

1. A method of hybridizing a first cotton variety with a second cotton variety comprising the steps of:
   (a) periodically applying to plants of said first cotton variety an isothiazole plant growth regulator, said regulator having the formula:

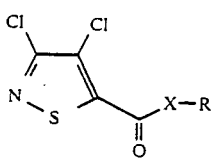

where X is oxygen, sulfur or

provided that when:
   (i) X is oxygen, R is: naphthyl; phenyl; phenyl substituted with 1 to 2 halogens, halomethyl, 1 to 2 lower alkyl groups of 1 to 4 carbon atoms, 1 to 2 lower alkyl groups of 1 to 4 carbon atoms substituted with fluoro, 1 to 2 methoxyl alkyl groups of 1 to 4 atoms, 1 to 2 methoxy alkyl groups of 1 to 4 carbon atoms substituted with fluoro, 1 to 2 nitro groups or trifluoro; ethoxyphenyl; ethoxyphenyl substituted with chloro or methoxy; ethyl thiophenyl; ethyl thiophenyl substituted with chloro or methoxy; cyclohexyl; cyclohexyl monosubstituted with a lower alkyl group of 1 to 4 carbon atoms; an alkenyl group of 2 to 4 carbon atoms; or a structure having the formula:

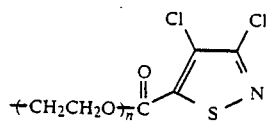

where n is from 3 to 6;
   (ii) X is

R is: phenyl; phenyl substituted with 1 to 2 nitro groups; or a pyridyl group; and
   (iii) X is sulfur, R is an alkylthioalkyl group in which each alkyl is of 1 to 4 carbon atoms;
   (b) monitoring the presence or absence and degree of burning of the bracts of said plants;
   (c) adjusting the amount and/or periodicity of application of said regulator in response to said monitoring; and
   (d) exposing said first cotton variety to pollen from said second cotton variety.

2. The method of claim 1 wherein the periodic application commences at least about two weeks prior to the first flowering of said plants and continues at least until about twelve weeks prior to harvest of the plants.

3. The method of claim 1 further comprising harvesting seed from said first cotton variety.

4. The method of claim 3 further comprising cultivating the seed to provide plants bearing cotton.

5. The method of claim 1 wherein said adjusting comprises either: the application of additional regulator, or irrigating the plants.

6. The method of claim 1 wherein said regulator is applied in an amount of from about 0.1 to about 2.0 pounds per acre.

7. The method of claim 1 wherein said adjusting results in finger burning of said bracts.

8. The method as defined in claim 1, 2, 3, 4, 5, 6, or 7 wherein the isothiazole regulator is selected from the group of compounds consisting essentially of Cyclohexyl 3,4-dichloro-5-isothiazolecarboxylate; Phenyl 3,4-dichloro-5-isothiazolecarboxylate; p-Chlorophenyl 3,4-dichloro-5-isothiazolecarboxylate; p-Tolyl 3,4-dichloro-5-isothiazolecarboxylate; -p-Anisyl 3,4-dichloro-5-isothiazolecarboxylate; 2-Naphthyl 3,4-dichloro-5-isothiazolecarboxylate; Poly(ethylene glycol)200 bis(3,4-dichloro-5-isothiazolecarboxylate); Poly(ethylene glycol) 1000 bis(3,4-dichloro-5-isothiazolecarboxylate); 3,4-Dichloro-5-isothiazolecarboxylate; 4-Methylcyclohexyl 3,4-dichloro-5-isothiazolecarboxylate; 3,3,5-Trimethylcyclohexyl 3,4-dichloro-5-isothiazolecarboxylate; 2-sec-Butyl-4,6-dinitrophenyl 3,4-dichloro-5-isothiazolecarboxylate; 3-Trifluoromethylphenyl 3,4-dichloro-5-isothiazolecarboxylate; 2,6-Dichloro-4-(fluorosulfonyl)phenyl 3,4-dichloro-5-isothiazolecarboxylate; S-(3-Propylthio)propyl 3,4-dichloro-5-isothiazolecarbothioate; 3,4-Dichloro-2',4'-dinitro-5-isothiazolecarboxylate; N-(2-Pyridyl)-3,4-dichloro-5-isothiazolecarboxylate; 4-Chloro-2-fluorosulfonylphenyl 3,4-dichloro-5-isothiazolecarboxylate; Allyl 3,4-dichloro-5-isothiazolecarboxylate; 2-(p-Methoxyphenoxy) ethyl 3,4-dichloro-5-isothiazolecarboxylate; 2-(p-Chlorophenylthio)ethyl 3,4-dichloro-5-isothiazolecarboxylate; and p-bromophenyl 3,4-dichloro-5-isothiazolecarboxylate.

9. A method of hybridizing a first cotton variety with a second cotton variety comprising the step of:
   (a) applying in a first application to plants of said first variety an amount of an isothiazole plant growth regulator sufficient to cause finger burning of the bracts of said plant without causing excessive burning thereof, said regulator having the formula:

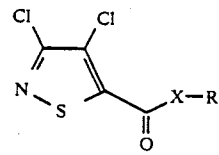

where X is oxygen, sulfur or

provided that when:
   (i) X is oxygen, R is: naphthyl; phenyl; phenyl substituted with 1 to 2 halogens, halomethyl, 1 to 2 lower alkyl groups of 1 to 4 carbon atoms, 1 to 2 lower alkyl groups of 1 to 4 carbon atoms substituted with fluoro, 1 to 2 methoxyl alkyl groups of 1 to 4 carbon atoms, 1 to 2 methoxy alkyl groups of 1 to 4 carbon atoms substituted with fluoro, 1 to 2 nitro groups or trifluoro; ethoxyphenyl; ethoxyphenyl substituted with chloro or methoxy; ethyl thiophenyl; ethyl thiophenyl substituted with chloro or methoxy; cyclohexyl; cyclohexyl monosubstituted with a lower alkyl group of 1 to 4 carbon atoms; an alkenyl group of 2 to 4 carbon atoms; or a structure having the formula:

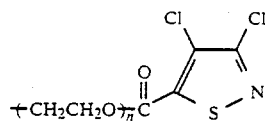

where n is from 3 to 6;
(ii) X is

R is: phenyl; phenyl substituted with 1 to 2 nitro groups; or a pyridyl group; and
(iii) X is sulfur, R is an alkylthioalkyl group in which each alkyl is of 1 to 4 carbon atoms;
(b) monitoring the presence of absence and degree of bract burning in said plants;
(c) periodically applying additional amounts of said regulator sufficient to maintain finger burning in the bracts without causing excessive burning thereof; and
(d) exposing said plants of said first variety to pollen of said second variety.

10. The method of claim 9 wherein the periodic application commences at least about two weeks prior to the first flowering of said plants and continues at least until about twelve weeks prior to harvest of the plants.

11. The method of claim 9 further comprising harvesting seed from the plants of said first variety.

12. The method of claim 11 further comprising cultivating said seeds to provide plants bearing cotton.

13. The method as defined in claim 9, 10, 11, or 12 wherein the isothiazole regulator is selected from the group of compounds consisting essentially of Cyclohexyl 3,4-dichloro-5-isothiazolecarboxylate; Phenyl 3,4-dichloro-5-isothiazolecarboxylate; p-Chlorophenyl 3,4-dichloro-5-isothiazolecarboxylate; p-Tolyl 3,4-dichloro-5-isothiazolecarboxylate; -p-Anisyl 3,4-dicloro-5-isothiazolecarboxylate; 2-Naphthyl 3,4-dichloro-5-isothiazolecarboxylate; Poly(ethylene glycol) 200 bis(3,4-dichloro-5-isothiazolecarboxylate); Poly(ethylene glycol) 1000 bis(3,4-dichloro-5-isothiazolecarboxylate); 3,4-Dichloro-5-isothiazolecarboxylate; 4-Methylcyclohexyl 3,4-dichloro-5-isothiazolecarboxylate; 3,3,5-Trimethylcyclohexyl 3,4-dichloro-5-isothiazolecarboxylate; 2-sec-Butyl-4,6-dinitrophenyl 3,4-dichloro-5-isothiazolecarboxylate; 3-Trifluoromethylphenyl 3,4-dichloro-5-isothiazolecarboxylate; 2,6-Dichloro-4-(fluorosulfonyl)phenyl 3,4-dichloro-5-isothiazolecarboxylate; S-(3-Propylthio)propyl 3,4-dichloro-5-dichloro-5-isothiazolecarboxylate; 3,4-Dichloro-2',4'-dinitro-5-isothiazolecarboxylate; N-(2-Pyridyl)-3,4-dichloro-5-isothiazolecarboxylate; 4-Chloro-2-fluorosulfonylphenyl 3,4-dichloro-5-isothiazolecarboxylate; Allyl 3,4-dichloro-5-isothiazolecarboxylate; 2-(p-Methoxyphenoxy) ethyl 3,4-dichloro-5-isothiazolecarboxylate; 2-(p-Chlorophenyl-thio)ethyl 3,4-dichloro-5-isothiazolecarboxylate; and p-bromophenyl 3,4-dichloro-5-isothiazolecarboxylate.

14. A method of rendering cotton plants male sterile while retaining substantial female fertility comprising:
providing isothiazole plant growth regulator to the plants in an amount effective to render the cotton plants male sterile while retaining substantial female fertility, including the steps of:
contacting said plants with a preselected amount of the isothiazole plant growth regulator, said regulator having the formula:

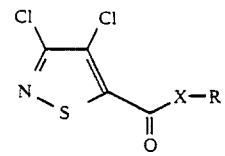

where X is oxygen, sulfur or

provided that when:
(i) X is oxygen, R is: naphthyl; phenyl; phenyl substituted with 1 to 2 halogens, halomethyl, 1 to 2 lower alkyl groups of 1 to 4 carbon atoms, 1 to 2 lower alkyl groups of 1 to 4 carbon atoms, substituted with fluoro, 1 to 2 methoxyl alkyl groups of 1 to 4 carbon atoms, 1 to 2 methoxy alkyl groups of 1 to 4 carbon atoms substituted with fluoro, 1 to 2 nitro groups or trifluoro; ethoxyphenyl; ethoxyphenyl substituted with chloro or methoxy; ethyl thiophenyl; ethyl thiophenyl substituted with chloro or methoxy; cyclohexyl; cyclohexyl monosubstituted with a lower alkyl group of 1 to 4 carbon atoms; or alkenyl group of 2 to 4carbon atoms; or a structure having the formula:

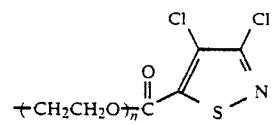

where n is from 3 to 6;
(i) X is

R is: phenyl; phenyl substituted with 1 to 2nitro groups; or a pyridyl group; and
(iii) X is sulfur, R is an alkylthioalkyl group in which each alkyl is of 1 to 4 carbon atoms monitoring the presence or absence and degree of burning of the bracts of the plants; and
adjusting the amount of regulator in response to said monitoring.

15. The method of claim 14 wherein said adjusting comprises either:
the application of additional regulator, or
irrigating the plants.

16. The method of claim 14 wherein said contacting is in an amount of from about 0.1 to about 2.0 pounds per acre.

17. The method of claim 14, 15, or 16 wherein the isothiazole regulator is selected from the group of compounds consisting essentially of Cyclohexyl 3,4-dichloro-5-isothiazolecarboxylate; Phenyl 3,4-dichloro-5-isothiazolecarboxylate; p-Chlorophenyl 3,4-dichloro-5-isothiazolecarboxylate; p-Tolyl 3,4-dichloro-5-isothiazolecarboxylate; -p-Anisyl 3,4-dicloro-5-isothiazolecarboxylate; 2-Naphthyl 3,4-dichloro-5-isothiazolecarboxylate; Poly(ethylene glycol)200 bis(3,4-dichloro-5-isothiazolecarboxylate); Poly(ethylene glycol) 1000 bis(3,4-dichloro-5isothiazolecarboxylate); 3,4-Dichloro-5-isothiazolecarboxylate; 4-Methylcyclohexyl 3,4-dichloro-5-isothiazolecarboxylate; 3,3,5-Trimethylcyclohexyl 3,4-dichloro-5-isothiazolecarboxylate; 2-sec-Butyl-4,6-dinitrophenyl 3,4-dichloro-5-isothiazolecarboxylate; 3-Trifluoromethylphenyl 3,4-dichloro-5-isothiazolecarboxylate; 2,6-Dichloro-4-(fluorosulfonyl)phenyl 3,4-dichloro-5-isothiazolecarboxylate; S-(3-Propylthio)propyl 3,4-dichloro-5-isothiazolecarboxylate; 3,4-Dichloro-2',4'-dinitro-5-isothiazolecarboxylate; N-(2-Pyridyl)-3,4-dichloro-5-isothiazolecarboxylate; 4-Chloro-2-fluorosulfonylphenyl 3,4-dichloro-5-isothiazolecarboxylate; Allyl 3,4-dichloro-5-isothiazolecarboxylate; 2-(p-Methoxyphenoxy) ethyl 3,4-dichloro-5-isothiazolecarboxylate; 2-(p-Chlorophenylthio)ethyl 3,4-dichloro-5-isothiazolecarboxylate; and p-bromophenyl 3,4-dichloro-5-isothiazolecarboxylate.

18. A method of rendering cotton plants male sterile while retaining substantial female fertility comprising:
providing an isothiazole plant growth regulator to the plants in a amount effective to render the cotton plants male sterile while retaining substantial female fertility, including the steps of:
contacting said plants with a preselected amount of the isothiazole plant growth regulator;
monitoring the presence or absence and degree of burning of the bracts of the plant; and
in response to said monitoring, either;
further contacting said plants with an additional amount of plant growth regulator or
irrigating the plants or
maintaining said contacting;
wherein said regulator is of the formula:

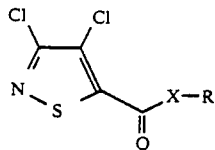

where X is oxygen, sulfur or

provided that when:
(i) X is oxygen, R is: naphthyl; phenyl; phenyl substituted with 1 to 2halogens, halomethyl, 1 to 2 lower alkyl groups of 1 to 4 carbon atoms, 1 to 2 lower alkyl groups of 1 to 4 carbon atoms substituted with fluoro, 1 to 2 methoxyl alkyl groups of 1 to 4 carbon atoms, 1 to 2 methoxy alkyl groups of 1 to 4 carbon atoms substituted with fluoro, 1 to 2 nitro groups or trifluoro; ethoxyphenyl; ethoxyphenyl substituted with chloro or methoxy; ethyl thiophenyl; ethyl thiophenyl substituted with chloro or methoxy; cyclohexyl; cyclohexyl monosubstituted with a lower alkyl group of 1 to 4 carbon atoms; an alkenyl group of 2 to 4 carbon atoms; or a structure having the formula:

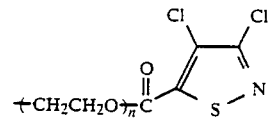

where n is from 3 to 6;
(ii) X is

R is: phenyl; phenyl substituted with 1 to 2 nitro groups; or a pyridyl group; and
(iii) X is sulfur, R is an alkylthioalkyl group in which each alkyl is of 1 to 4 carbon atoms.

19. The method of claim 18 wherein said preselected amount is from about 1.0 to 2.0 pounds per acre.

20. The method of claim 18 wherein said amount is preselected to result in bract finger burning in said plants in from about 3 to about 5 days.

21. The method of claim 18 wherein said further contacting is in response to a monitored condition of no burning of the bracts and said irrigation is in response to a condition of excessive burning of the bracts.

22. The method as defined in claim 18, 19, 20 or 21 wherein the isothiazole regulator is selected from the group of compounds consisting essentially of Cyclohexyl 3,4-dichloro-5-isothiazolecarboxylate; Phenyl 3,4-dichloro-5-isothiazolecarboxylate; p-Chlorophenyl 3,4-dichloro-5-isothiazolecarboxylate; p-Tolyl 3,4-dichloro-5-isothiazolecarboxylate; -p-Anisyl 3,4-dicloro-5-isothiazolecarboxylate; 2-Naphthyl 3,4-dichloro-5-isothiazolecarboxylate; Poly(ethylene glycol)200 bis(3,4-dichloro-5isothiazolecarboxylate); Poly(ethylene glycol) 1000 bis(3,4-dichloro-5isothiazolecarboxylate); 3,4-Dichloro-5-isothiazolecarboxylate; 4-Methylcyclohexyl 3,4-dichloro-5-isothiazolecarboxylate; 3,3,5-Trimethylcyclohexyl 3,4-dichloro-5-isothiazolecarboxylate; 2-sec-Butyl-4,6-dinitrophenyl 3,4-dichloro-5-isothiazolecarboxylate; 3-Trifluoromethylphenyl 3,4-dichloro-5-isothiazolecarboxylate; 2,6-Dichloro-4-(fluorosulfonyl)phenyl 3,4-dichloro-5-isothiazolecarboxylate; S-(3-Propylthio)propyl 3,4-dichloro-5-isothiazolecarbothioate; 3,4-Dichloro-2',4'-dinitro-5-isothiazolecarboxylate; N-(2-Pyridyl)-3,4-dichloro-5-isothiazolecarboxylate; 4-Chloro-2-fluorosulfonylphenyl 3,4-dichloro-5-isothiazolecarboxylate; Allyl 3,4-dichloro-5isothiazolecarboxylate; 2-(p-Methoxyphenoxy) ethyl 3,4-dichloro-5-isothiazolecarboxylate; 2-(p-Chlorophenylthio)ethyl 3,4-dichloro-5-isothiazolecarboxylate; and p-bromophenyl 3,4-dichloro-5-isothiazolecarboxylate.

23. A method for rendering cotton plants male sterile for substantially an entire growing season comprising:
providing an isothiazole plant growth regulator to the cotton plants in an amount effective to render the cotton plants male sterile while retaining substantial female fertility for an entire growing season including the steps of:

periodically applying to the plants preselected amounts of isothiazole plant growth regulator;

monitoring the presence or absence and degree of burning of the bracts of the plant; and adjusting the amount and/or periodicity of application of said regulator in response to said monitoring, the periodic application commencing at least about two weeks prior to the first flowering of said plants in said cotton season and continuing at least until about twelve weeks prior to harvest of the plants, wherein said regulator is of the formula:

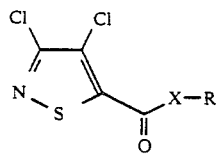

where X is oxygen, sulfur or

provided that when:
(i) X is oxygen, R is: naphthyl; phenyl; phenyl substituted with 1 to 2 halogens, halomethyl, 1 to 2 lower alkyl groups of 1 to 4 carbon atoms, 1 to 2 lower alkyl groups of 1 to 4 carbon atoms substituted with fluoro, 1 to 2 methoxyl alkyl groups of 1 to 4 carbon atoms, 1 to 2 methoxy alkyl groups of 1 to 4 carbon atoms substituted with fluoro, 1 to 2 nitro groups or trifluoro; ethoxyphenyl; ethoxyphenyl substituted with chloro or methoxy; ethyl thiophenyl; ethyl thiophenyl substituted with chloro or methoxy; cyclohexyl; cyclohexyl monosubstituted with a lower alkyl group of 1 to 4 carbon atoms; an alkenyl group of 2 to 4 carbon atoms; or a structure having the formula:

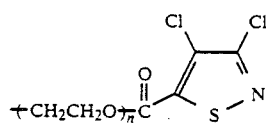

where n is from 3 to 6;
(ii) X is

R is: phenyl; phenyl substituted with 1 to 2 nitro groups; or a pyridyl group; and
(iii) X is sulfur, R is an alkylthioalkyl group in which each alkyl is of 1 to 4 carbon atoms.

24. The method of claim 23 wherein said adjusting results in finger burning of said bracts.

25. The method of claim 23 wherein said application is in the amount of from about 0.1 to about 2.0 pounds per acre.

26. The method as defined in claim 23, 24 or 25 wherein the isothiazole regulator is selected from the group of compounds consisting essentially of Cyclohexyl 3,4-dichloro-5-isothiazolecarboxylate; Phenyl 3,4-dichloro-5-isothiazolecarboxylate; p-Chlorophenyl 3,4-dichloro-5-isothiazolecarboxylate; p-Tolyl 3,4-dichloro-5-isothiazolecarboxylate; -p-Anisyl 3,4-dicloro-5-isothiazolecarboxylate; 2-Naphthyl 3,4-dichloro-5-isothiazolecarboxylate; Poly(ethylene glycol)200 bis(3,4-dicloro-5-isothiazolecarboxylate); Poly(ethylene glycol) 1000 bis(3,4-dichloro-5-isothiazolecarboxylate); 3,4-Dichloro-5-isothiazolecarboxylate; 4-Methylcyclohexyl 3,4-dichloro-5-isothiazolecarboxylate; 3,3,5-Trimethylcyclohexyl 3,4-dichloro-5-isothiazolecarboxylate; 2-sec-Butyl-4,6-dinitrophenyl 3,4-dichloro-5-isothiazolecarboxylate; 3-Trifluoromethylphenyl 3,4-dichloro-5-isothiazolecarboxylate; 2,6-Dichloro-4-(fluorosulfonyl)phenyl 3,4-dichloro-5isothiazolecarboxylate; S-(3-Propylthio)propyl 3,4-dichloro-5-isothiazolecarboxylate; 3,4-Dichloro-2',4'-dinitro-5-isothiazolecarboxylate; N-(2-Pyridyl)-3,4-dichloro-5-isothiazolecarboxylate; 4-Chloro-2-fluorosulfonylphenyl 3,4-dichloro-5-isothiazolecarboxylate; Allyl 3,4-dichloro-5-isothiazolecarboxylate; 2-(p-Methoxyphenoxy) ethyl 3,4-dichloro-5-isothiazolecarboxylate; 2-(p-Chlorophenylthio)ethyl 3,4-dichloro-5-isothiazolecarboxylate; and p-bromophenyl 3,4-dichloro-5-isothiazolecarboxylate.

27. A method for achieving male sterility in cotton plants comprising:

applying in a first application to said cotton plants an amount of an isothiazole plant growth regulator sufficient to cause finger burning of the bracts of said cotton plants but which is not so much as to cause excessive burning thereof; and periodically applying additional amounts of said regulator to said plants sufficient to maintain finger burning without achieving excessive burning of the bracts, wherein said regulator is of the formula:

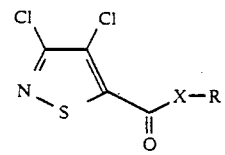

where X is oxygen, sulfur or

provided that when:
(i) X is oxygen, R is: naphthyl; phenyl; phenyl substituted with 1 to 2 halogens, halomethyl, 1 to 2 lower alkyl groups of 1 to 4 carbon atoms, 1 to 2 lower alkyl groups of 1 to 4 carbon atoms substituted with fluoro, 1 to 2 methoxyl alkyl groups of 1 to 4 carbon atoms, 1 to 2 methoxy alkyl groups of 1 to 4 carbon atoms substituted with fluoro, 1 to 2 nitro groups or trifluoro; ethoxyphenyl; ethoxyphenyl substituted with chloro or methoxy; ethyl thiophenyl; ethyl thiophenyl substituted with chloro or methoxy; cyclohexyl; cyclohexyl monosubstituted with a lower alkyl group of 1 to 4 carbon atoms; an alkenyl group of 2 to 4 carbon atoms; or a structure having the formula:

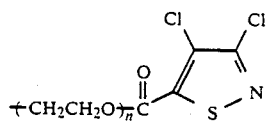

where n is from 3 to 6;
(ii) X is

R is: phenyl; phenyl substituted with 1 to 2 nitro groups; or a pyridyl group; and
(iii) X is sulfur, R is an alkylthioalkyl group in which each alkyl is of 1 to 4 carbon atoms.

28. The method of claim 27 wherein said period is about two weeks.

29. The method of claim 27 wherein said first application is about two weeks prior to first flowering of the plants.

30. The method as defined in claim 27, 28 or 29 wherein the isothiazole regulator is selected from the group of compounds consisting essentially of Cyclohexyl 3,4-dichloro-5-isothiazolecarboxylate; Phenyl 3,4-dichloro-5-isothiazolecarboxylate; p-Chlorophenyl 3,4-dichloro-5-isothiazolecarboxylate; p-Tolyl 3,4-dichloro-5-isothiazolecarboxylate; -p-Anisyl 3,4-dicloro-5-isothiazolecarboxylate; 2-Naphthyl 3,4-dichloro-5-isothiazolecarboxylate; Poly(ethylene glycol)200 bis(3,4-dichloro-5-isothiazolecarboxylate); Poly(ethylene glycol) 1000 bis(3,4-dichloro-5-isothiazolecarboxylate); 3,4-Dichloro-5-isothiazolecarboxylate; 4-Methylcyclohexyl 3,4-dichloro-5-isothiazolecarboxylate; 3,3,5-Trimethylcyclohexyl 3,4-dichloro-5-isothiazolecarboxylate; 2-sec-Butyl-4,6-dinitrophenyl 3,4-dichloro-5-isothiazolecarboxylate; 3-Trifluoromethylphenyl 3,4-dichloro-5-isothiazolecarboxylate; 2,6-Dichloro-4-(fluorosulfonyl)phenyl 3,4-dichloro-5isothiazolecarboxylate; S-(3-Propylthio)propyl 3,4-dichloro-5-isothiazolecarboxylate; 3,4-Dichloro-2',4'-dinitro-5-isothiazolecarboxylate; N-(2-Pyridyl)-3,4-dichloro-5-isothiazolecarboxamide; 4-Chloro-2-fluorosulfonylphenyl 3,4-dichloro-5-isothiazolecarboxylate; Allyl 3,4-dichloro-5-isothiazolecarboxylate; 2-(p-Methoxyphenoxy) ethyl 3,4-dichloro-5-isothiazolecarboxylate; 2-(p-Chlorophenylthio)ethyl 3,4-dichloro-5-isothiazolecarboxylate; and p-bromophenyl 3,4-dichloro-5-isothiazolecarboxylate.

* * * * *